United States Patent [19]

DiFrancesco

[11] Patent Number: 5,141,857
[45] Date of Patent: Aug. 25, 1992

[54] PURIFICATION OF Q BETA REPLICASE

[75] Inventor: Robert A. DiFrancesco, Auburn, Mass.

[73] Assignee: Gene-Trak Systems, Framingham, Mass.

[21] Appl. No.: 364,306

[22] Filed: Jun. 9, 1989

[51] Int. Cl.$^5$ ............................................. C12D 19/34
[52] U.S. Cl. ................................... 435/91; 424/94.5; 435/194; 435/220
[58] Field of Search ................ 435/194, 849, 91, 220; 424/94.61

[56] References Cited

U.S. PATENT DOCUMENTS 4,693,978  9/1987  Stetter et al. ...................... 435/199
4,786,600  11/1988  Kramer et al.

OTHER PUBLICATIONS

N. V. Fedoroff, In: Dissertation Abstracts Int'l., Sci. and Eng., 34(1):110B-111B (1973).
J. Yamauchi, Patent Abstracts of Japan, vol. 10, No. 23, C-325 (abstract of JP 60-176584) (1984).
K. Kobayashi, Patent Abstracts of Japan, vol. 8, No. 77, C-218, (abstract JP 57-111364 (1982).
K. Kobayashi, Patent Abstracts of Japan, vol. 7, No. 273, C-198 (abstract JP 57-33969) (1982).
Lizardi et al Bio/technology (vol. 6) pp. 1197-1201 1988.
Hill and Blumenthal, Nature 301:350-352 (1983).
Banerjee et al., J. Mol. Biol. 45:181-193 (1986).
Schattner et al., J. Mol. Biol. 117:877-907 (1977).
Eoyang, et al. In: Proc in Nucleic Acids Research, vol. 2, pp. 829-839 (Cantoni & Davies, eds.) Harper & Row, N.Y., 1971.
Cooper, "The Tools of Biochemistry" ch. 4, pp. 136-151 1977.
D. R. Mills, Journal of Molecular Biology, 200:489-500.
R. Kamen, Biochimica and Biophysica Acta, 262:88-100 (1972).
L. Eoyang and J. T. August, In: Procedures In Nucleic Acids Research, Vol. 2, pp. 829-839, (Cantoni and Davies, eds.) Harper and Row, New York (1971).
T. Blumenthal and G. G. Carmichael, Annual Review of Biochemistry, 48:525-548 (1979).
D. R. Mills et al., Science, 180:916-927 (1973).
M. Sumper and R. Luce, Proc. Nat'l. Acad. Sci. USA, 72:162-166 (1975).
D. Hill and T. Blumenthal, Nature, 301:305-352 (1983).
C. K. Biebricher et al., Nature, 321:89-91 (1986).

Primary Examiner—Douglas W. Robinson
Assistant Examiner—Jane Williams
Attorney, Agent, or Firm—Hamilton, Brooks, Smith & Reynolds

[57] ABSTRACT

A process of producing highly pure, Q Beta replicase having a high level of activity is described. The present process allows isolation of Q Beta replicase from recombinant bacteria containing a clone of a phage DNA encoding the 65,000 weight subunit of Q Beta replicase. The present process provides an efficient method for producing pure Q Beta replicase which can readily be scaled up to commercial production levels.

6 Claims, 2 Drawing Sheets 1 2 3
| | KDal |
|---|---|
| — | 97.4 |
| — | 66 |
| — | 43 |
| — | 31 |
| — | 21 |
| — | 14 |
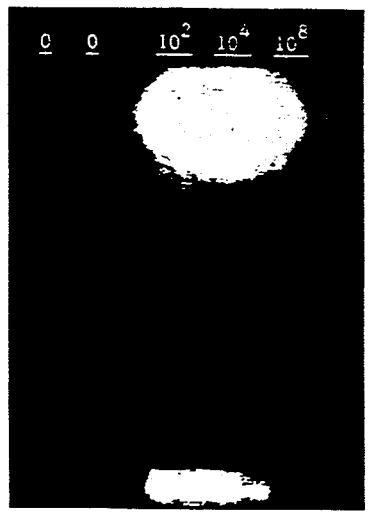
Fig. 1
Marker # Input Molecules
-MDV-Fal-St RNA
-DS MDV-Fal-St
Fig. 2
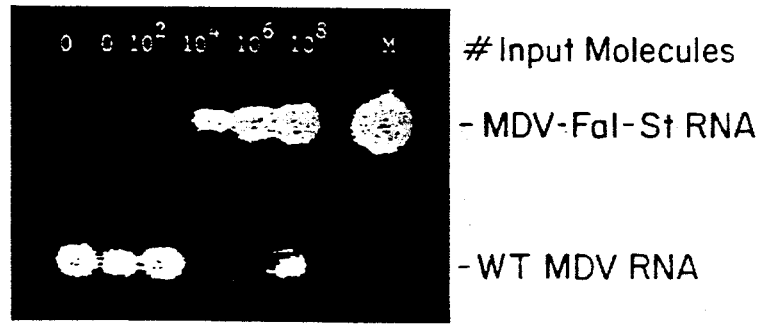
Input Molecules
-MDV-Fal-St RNA
-WT MDV RNA
Fig. 3

PURIFICATION OF Q BETA REPLICASE

DESCRIPTION

Background

Q Beta replicase is an RNA dependent RNA polymerase that is produced in *E. coli* as a result of infection by the bacteriophage Q Beta. Q Beta replicase is composed of one phage-encoded polypeptide of molecular weight 65,000, and three host-encoded polypeptides of molecular weight 70 000, 45,000, and 35,000. These host-encoded polypeptides are, respectively: 30 S ribsomal protein S1, and protein synthesis elongation factors EF-Tu and EF-Ts. T. Blumenthal and G. Carmichael, *Ann. Rev. Biochem.*, 28:525-548 (1979).

Q Beta replicase autocatalytically replicates some specific types of RNA known as variants *in vitro*. This RNA can be amplified exponentially, to produce quantities of RNA which are then used in bioassays. For example, midivariant (MDV) RNA produced by Q Beta replicase in such an amplification system can be tagged with biotin to form biotinylated RNA which combines with avidin to form an adduct useful as a reporter for a variety of replication-assisted bioassays for antibodies or nucleic acids. B. C. F. Chu et al., *Nucleic Acids Res.*, 14:5591 (1986); E. A. Miele et al., *J. Mol. Biol.*, 171:281 (1983).

Q Beta replicase is generally obtained and isolated from Q Beta phage-infected cells. Eoyang and August report a complex scheme for isolating Q Beta replicase which consists of: 1) alumina extraction of bacteriophage infected cells, 2) polyethylene glycol (PEG)-dextran phase partitioning, 3) ammonium sulfate precipitation, 4) phosphocellulose column chromatography, 5) QAE-Sephadex column chromatography, 6) hydroxylapatite column chromatography, and 7) Bio-Gel A.0.5 m column chromatography. Eoyang, L. and August, J. L. *Proc. Nucleic Acic Res.*, 829 (1972). Kamen and others also describe schemes for obtaining Q Beta replicase, which are variations of the above. Kamen, R. *Biochem Biophys. Acta.* 262: 88-100 (1972); Sumper. M. and Luce, R. *Proc. Nat. Acad. Sci. USA*, 162.166 (1975). Presently, available methods of obtaining Q Beta replicase have several important limitations: the resulting product is not sufficiently pure (i.e., contaminated with MDV$^{-1}$ RNA), the procedures are complex and labor intensive, and they cannot be readily scaled up to a production level to produce large quantities needed for use in commercial assay systems. The use of alumina extraction and PEG-dextran phase partitioning in the initial processing steps places severe limitations on the scale of the process.

SUMMARY OF THE INVENTION

The present invention relates to a method or process for purifying Q Beta replicase from cells which produce the enzyme and to highly purified Q Beta replicase, obtained by the present method, which is essentially free of midivariant or other template RNA contamination (i.e., substantially pure Q B replicase). The method is a four-step scheme which consists of 1) disrupting the cells to form a crude cell lysate; 2) contacting the cell lysate with a polymeric agent which selectively precipitates nucleic acids; 3) separating the enzyme by chromatography; and 4) purifying the enzyme by chromatography.

The subject method has several advantages that presently-available methods do not offer. First, because the subject method includes a step of disrupting the cells, kilogram amounts of cell paste can be processed. In contrast, presently-available processes, such as those including alumina extraction, are only useful for small amounts, (i.e., about 100-200 grams) of cell paste. Second, because it includes a precipitation step, the present method does not include a PEG-dextran phase partitioning step, which is the major rate limiting step in other processes. The use of precipitation in the presence of sodium chloride in the present method not only increases the amount of Q Beta replicase that is extracted from the cells, but also eliminates several inhibitors of the enzyme that are present in crude Q Beta replicase extracts made by other processes. Third, through use of the present purification process, high yields of the enzyme result. Fourth, the replicase produced has a high level of specific activity, and nearly homogeneous (nearly pure) enzyme is obtained. That is, the yield of Q Beta replicase from the present process is nearly 10-fold higher than yields from previously-available methods, the specific activity of the product is nearly 8-fold higher than the specific activity of the product of previously available methods; and Q Beta replicase produced by the present method is nearly homogeneous, while enzyme purified by prior art methods is only about 50% pure. Fifth, the present process is simple and can ba readily scaled up. For example, it can be used to produce highly purified Q Beta replicase in sufficient quantities for use in a commercial Q Beta amplification system.

BRIEF DESCRIPTION OF THE FIGURES

FIG. 1 shows an SDS:PAGE gel comparing samples of purified Q Beta replicase. Samples of reduced and denatured Q Beta replicase were run on denaturing 10-15% polyacrylamide gradient gels, and stained with Coomassie blue. Lane 1: Q Beta replicase purified by the method of Eoyang and August, *Proc. Nucleic Acid Res.* 2:829 (1972). Lane 2: Q Beta replicase purified by the present process. Lane 3: Molecular weight markers.

FIG. 2 shows denaturing polyacrylamide gel analysis of RNA products synthesized through the use of Q Beta replicase purified by the present process. Lane 1: 0 input molecules; Lane 2: $10^2$ molecules; Lane 3: $10^4$ molecules; Lane 4: $10^8$ molecules; and Lane 5: MDV-FAL-St RNA marker.

FIG. 3 shows a denaturing polyacrylamide gel of RNA products synthesized by Q Beta replicase purified by the method of Eoyang and August, ibid. Lanes 1 and 2: 0 input molecules; Lane 3: $10^2$ molecules; Lane 4: $10^4$ molecules; Lane 5: $10^6$ molecules; Lane 6: $10^8$ molecules; and Lane 7: MDV-Fal-St.

DETAILED DESCRIPTION OF THE INVENTION

Figure 4:
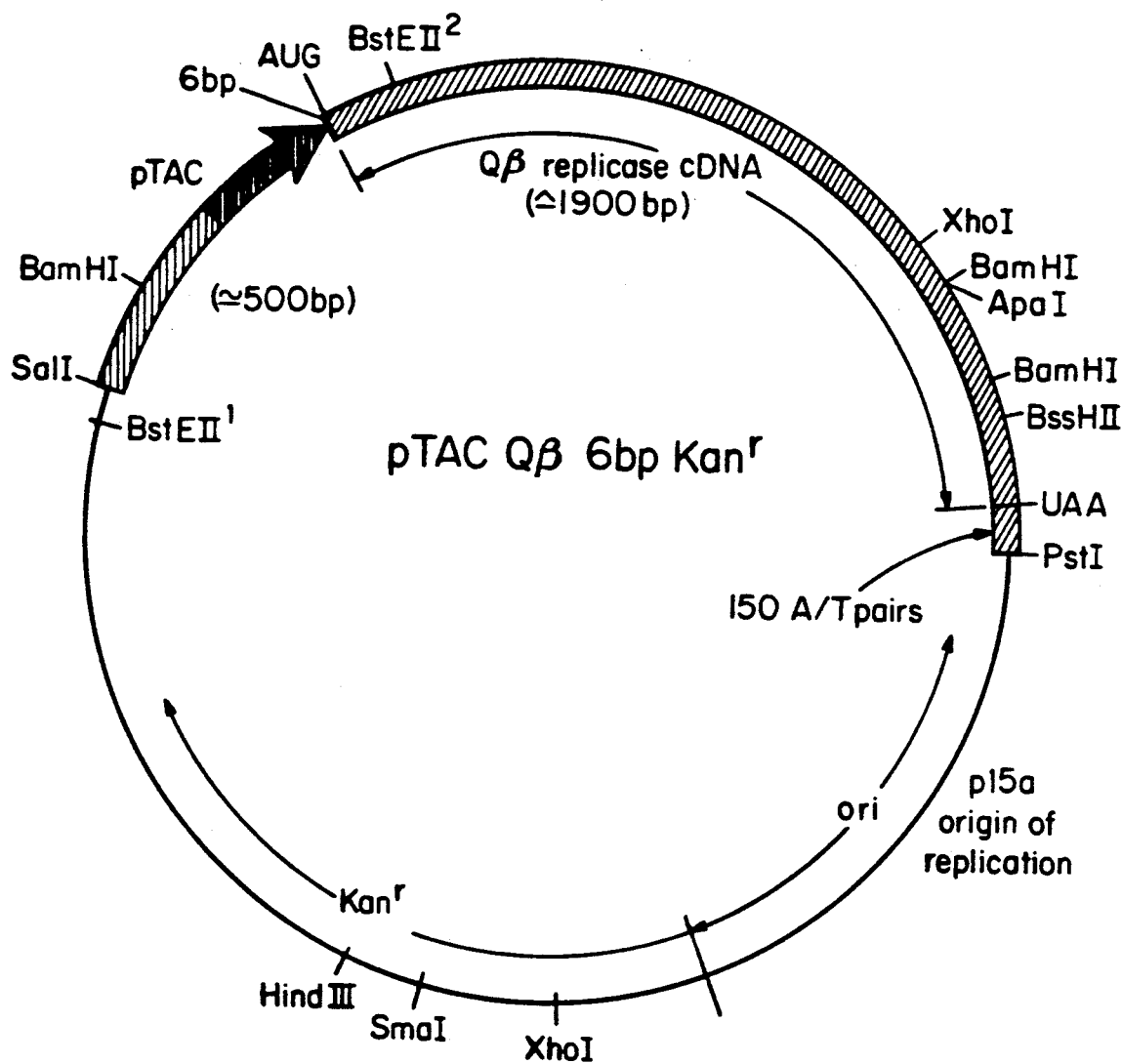
FIG. 4 is a schematic representation of plasmid pTAC QB 6Bp Kan$^r$, which contains the Q Beta replicase gene under the control of the tac promotor.

The present invention relates to a process or method for purifying Q Beta replicase and to essentially pure or homogeneous Q Beta replicase. The present method is useful for obtaining from cells which produce Q Beta replicase (e.g., cells containing and expressing a recombinant construct as well as phage-infected cells), Q Beta replicase which is substantially free of contaminants, such as midi-variant RNA, Q Beta RNA or other template. As used herein, Q Beta replicase is said to be "substantially free" of contaminants if, when it is incubated in standard amplification assay buffer which does not contain any additional RNA template, no detectable RNA synthesis occurs.

The present process has four general steps:
1) disruption of Q Beta replicase-producing cells, to produce a (homogeneous) cell lysate;
2) separation of the enzyme from the cell lysate, which is carried out, for example, by contacting the suspension with an amine, such as polyethyleneimine resulting in precipitation of nucleic acids and nucleic acid processing enzymes bound to them, and, therefore, initial separation of Q Beta replicase from unwanted cellular materials;
3) contact of the supernatant produced in step (2) containing the enzyme with a cationic resin, such as Q Sepharose; and
4) contact of the eluant produced in Step (3) with an anionic resin, such as S Sepharose.

Through use of the present method, Q Beta replicase of greater purity than can be obtained through previously known methods is produced For example, Q Beta replicase shown to be more than 95% pure, as judged by SDS polyacrylamide gel electrophoresis (PAGE), has been obtained by the present method.

The present process is generally carried out at cold room temperatures (about 4° C.) to prevent the enzyme from denaturing, although it is not necessary to do so. In the first step of the present process, cells which produce Q Beta replicase are disrupted. Any calls which produce Q Beta replicase can be used as a source of Q Beta replicase. For example, the present method can be used to obtain Q Beta replicase from bacterial cells which have been infected with the Q Beta bacteriophage. Haruna and Spiegelman, *Proc. Nat'l Acad. Sci. U.S.A.*, 54:579 587 (1965). It can also be used to obtain Q Beta replicase from cells which contain a clone of the Q Beta replicase phage subunit, which contains the Q Beta replicase gene under the control of an appropriate promoter. The present method will now be described as it has been used to purify Q Beta replicase from bacterial cells (*E. coli*) expressing the cloned gene for the Q Beta replicase phage subunit (constructed by D. Mills, Downstate Medical Center, Brooklyn, NY) under the control of the promoter. It is to be understood, however, that the present method can also be used to purify Q Beta replicase from other cells in which it is produced. Plasmid pTAC QB 6Bp Kan$^r$, which contains the Q Beta replicase gene under the control of the promoter is represented schematically in FIG. 4. D. R. Mills, *J. Mol. Biol.*, 200:489–500 (1988) U.S. Pat. No. 4,786,600.

Q Beta replicase-producing cells are suspended in an aqueous medium such as a buffer (e.g., Tris buffer), and treated to disrupt the cells Cells can be disrupted by enzymatic methods (e.g., with lysozyme) or by physical methods. Treatment which physically disrupts the cells is generally by mechanical means, such as sonication or homogenization. Such treatment causes the cell membrane to rupture, resulting in release of the contents of the cells into the suspending medium, forming a cell lysate.

In the second step of the present process, nucleic acids in the cell lysate are selectively removed for example by contacting the lysate with an agent which can selectively precipitate the nucleic acids present in the lysate. In this step, the cell lysate is contacted with the agent under conditions sufficient to cause precipitation of nucleic acids and nucleic acid processing enzymes while retaining Q Beta replicase in the supernatant. A particularly useful agent for this purpose is polyethylenimine (PEI). However, other agents which precipitate nucleic acids, such as streptomycin sulfate, can be used. The precipitation step is necessary to remove MDV$^-$RNA, and other nucleic acids from the cell lysate. Once precipitation is completed, the precipitate containing the PEI and other cell debris is separated from the mixture, by centrifugation, for example, and discarded. Q Beta replicase is present in the resulting supernatant, which is subsequently treated in such a manner, as described below, that substantially pure Q Beta replicase is obtained.

In the third step of the present process, the supernatant is diluted as needed (e.g., with a neutral buffer, such as Tris buffer). The diluted material is then applied to a cationic chromatography resin which binds Q Beta replicase enzyme The resin is generally contained In a column. Q Sepharose is a particularly useful resin for this purpose. However, other cationic resins, for example, QAE Sephadex, can also be used. After the enzyme has been loaded onto the resin, the resin is washed with several column volumes of a neutral buffer, such as Tris, containing a low concentration of a salt, such as NaCl. Once washing is complete, the enzyme is eluted from the column using a salt gradient, which ranges, for example, from about 100 to about 400 mM NaCl, in Tris buffer. The fractions are collected, and tested for the presence of the enzyme (e.g., by using an activity assay, such as the Poly C assay described in the Exemplification). Fractions are selected in order to minimize contaminants in the product. Preferably, the fractions showing the highest incorporation rate (the "peak activity" fractions) are pooled prior to the fourth step.

In the fourth step of the present process, the pooled fractions are contacted with an anionic chromatography resin. S Sepharose is a particularly useful resin for this purpose. The resin is preferably contained in a column. The pooled fraction is diluted as needed to lower the salt concentration (e.g., with the Tris buffer) and then loaded onto the resin. Once all of the fraction has been loaded onto the column, the column is washed, and then eluted with a salt gradient, as in the third step. The eluant is assayed to determine which fractions contain the peak enzyme activity.

Q Beta replicase obtained by this process is substantially homogeneous, and has been shown to be free of MDV$^{-1}$ RNA and to be more than 95% pure, as measured by SDS PAGE. As described below and in the Exemplification, the present method has been used to obtain such substantially pure Q Beta replicase. The present method can also be modified, however, to produce "less pure" enzyme (i.e., Q Beta replicase in combination with a limited quantity of other proteins), if desired. This can be effected by changing (shortening) the length of the chromatography column used, by increasing the quantity of materials loaded on a column, or by using "step" gradients rather than linear gradients. The process is conducive to scale-up to commercial production levels. The Q Beta replicase recovered from the last step of the method is highly active, and efficiently replicates midivariant (MDV) RNA templates in vitro In one embodiment of the present method, a culture of *E. coli* cells infected with Q Beta replicase phage or cells containing a subunit clone of the phage DNA encoding the 65,000 mw subunit of the enzyme is used.

The E. coli cells were transformed by a plasmid vector which contains the Q Beta replicase gene under the control of the tac promoter. The plasmid, designated pTAC QB 6Bp Kan, is shown schematically in FIG. 4. E. coli cells transformed by the plasmid produce Q Beta replicase. D. R. Mills, J. Mol. Biol. 200:489-500 (1988). The cells are suspended in a buffer or neutral salt solution which contains 50 mM Tris.HCl (pH 7.8), 55 mM MgCl$_2$, 5 mM 2.mercaptoethanol, 1 mM EDTA and 500 mM NaCl. This step, and all of the subsequent steps in the process are carried out at 4° C. The cells are disrupted by subjecting the cell suspension to homogenization, for example, in a Matlin Gaulin homogenizer, to form a crude cell lysate. The lysate is then contacted with 10% (w/v) polyethyleneimine (PEI), causing precipitation of the fraction containing MDV$^{-1}$ RNA. The precipitate and supernatant (which contains the Q Beta replicase) are separated by centrifugation. The supernatant is diluted with a buffer containing 50 mM Tris-HCl (pH 7.8), 5 mM MgCl$_2$, 5 mM 2.mercaptoethanol and 1 mM EDTA. The diluted solution is then contacted with Q Sepharose resin, which binds Q Beta replicase. The column is eluted with a salt gradient containing from about 100 to 400 mM NaCl and the fractions collected and assayed for Q Beta replicase activity. The fractions containing Q Beta replicase are pooled, diluted with the same dilution buffer, and contacted with S Sepharose resin. The Q Beta replicase selectively binds to the S Sepharose resin, thereby making it possible to separate the enzyme from other components. Q Beta replicase is eluted from the resin using a salt gradient, as above. Enzyme is obtained in high purity by this process.

The use of PEI precipitation followed by Q Sepharose and S Sepharose column chromatography produces nearly homogeneous enzyme. Other procedures require several additional steps to achieve the same level of purity, with a lower overall yield. A comparison of Q Beta replicase produced by the present process to enzyme produced by the process of Eoyang, ibid, and August is shown in Table 1.

TABLE 1

Comparison of Q Beta Replicase Purified by the Method of Eoyang and August Versus Present

| Method Process | U/ml | Total Units | mg/ml | Total mg | U/mg |
|---|---|---|---|---|---|
| Eoyang and August Method* | 173 | 1038 | 1.2 | 7.8 | 144 |
| Present Method# | 670 | 20,100 | 0.59 | 17.7 | 1130 |

*Prepared from 200 g of phage-infected cells
Prepared from 50 g of E. coli that contain the Q Beta phage subunit gene under the control of the tac promoter A particularly valuable aspect of this process is that it yields enzyme that is essentially free of MDV$^{-1}$ RNA, whereas replicase purified by the method of Eoyang and August is contaminated with MDV$^{-1}$ RNA.

The enzyme obtained through use of the present method efficiently replicates Q Beta replicase templates, such as MDV RNA. Thus, the enzyme is useful in bioassay systems (e.g., to produce MDV RNA for use as a reporter group, as described by Chu et al. B.C.F. Chu et al., Nucleic Acids Res., 14:5591 (1986)). Q Beta replicase produced by the present process is also useful in systems for amplifying RNA. The present enzyme, which is free of RNA contaminants and can be more than 95% pure (as judged by SDS:PAGE), is particularly useful in amplification and bioassay systems.

The invention is illustrated by the following exemplification, which is not intended to be limiting in any way.

EXEMPLIFICATION

*Purification of Q Beta Replicase from Phage-Infected E. Coli Cells*

One hundred (100 g) grams of recombinant E. coli cells containing the cloned gene for the Q Beta replicase phage subunit under the control of the tac promoter was used as the source of Q Beta replicase.

The following procedure was carried out in a cold room (4° C.), and in an RNA-free environment, using sterile buffers to minimize contamination with MDV.1 RNA. The E. coli cells were suspended in a one liter beaker in 2.5 volumes of a solution containing 50 mM Tris-HCl buffer, (pH 7.8), 55 mM MgCl$_2$, 5 mM 2.mercaptoethanol, 1 mM (ethylenediaminetetraacetic acid) EDTA and 500 mM NaCl. A clean stir bar was added and the contents of the beaker were stirred at 4° C. until the suspension was homogeneous One half of the cell suspension was transferred to a Rosett sonicating cell (250 ml Heat Systems-Ultrasonics) and the cell was placed in an ice water bath. The remainder of the cell suspension was kept on ice.

The cell suspension was sonicated 4 times, 2 minutes each time, at an output control setting of 7. After each 2 minute interval, the temperature of the suspension increased from 4° C. to about 10°-12° C. The cell suspension was allowed to cool down to 6° C. or less before resuming sonication. After sonication was complete, the volume of the sonicated cell suspension was measured. The suspension was transferred to a clean 1 L beaker and placed on ice. The procedure was repeated with the remainder of cell suspension.

A clean stir bar was added to the beaker containing sonicated cell suspension and the contents stirred on a stir plate at 4° C. 0.03 volumes of 10% polyethyleneimine (w/v) (Aldrich) was gradually added to the cell homogenate.

After all the polyethyleneimine was added, the suspension was stirred for an additional 15 minutes.

The contents of the beaker were transferred to two 250 ml polypropylene centrifuge bottles and centrifuged in a sorvall GSA rotor for 30 minutes at 10,000 rpm at 4° C. The clear supernatant was removed from the pellet material. The volume of the supernatant was measured and transferred to a clean 2 L beaker.

The supernatant was diluted with 4 volumes of the solution of 50 mM Tris-HCl (pH 7.8) 5 mM MgCl$_2$, 5 mM 2.mercaptoethanol, 1 mM EDTA, and applied in a concentration of 30 mg of protein per ml of resin to an equilibrated 220 ml Q Sepharose column (Q Sepharose Fast Flow resin, Pharmacia) at a flow rate of 400-450 ml/hr. A UV-1 monitor (Pharmacia, 280 nm filter) was set at a AUFS of 2.0 and the chart speed of 0.2 mm/min.

While the enzyme was being loaded onto the column, the supernatant fraction was assayed for Q Beta replicase activity using the Poly C assay (described below).

After all of the enzyme had been loaded onto the the column was washed with a solution of 50 mM Tris-HCl (pH 7.8), 5 mM MgCl$_2$, 5 mM 2.mercaptoethanol, 1 mM EDTA, and 100 mM NaCl, at a flow rate of 400-450 ml/hr. The column was washed until the UV absorbance decreased to less than 0.4 (4.6 column volumes).

A 10 column-volume (2×1100 ml) gradient was prepared ranging from 100-400 mM NaCl in 50 mM Tris.HCl (pH 7.8), 5 mM MgCl$_2$, 5 mM 2.mercaptoethanol, 1 mM EDTA, and the gradient was run at a flow rate of 200–225 ml/hr. Fractions of 22 ml were collected. The chart speed of the recorder was increased to 0.5 mm/min.

To minimize the risk of contaminating the fractions with MDV RNA, 0.1–0.2 ml aliquots of the fractions to be assayed were removed using sterile 1 ml pipettes and transferred to sterile 1.5 ml microcentrifuge tubes.

The Q Sepharose fractions were assayed for Q Beta replicase activity using the Poly C assay.

The peak replicase fractions were assayed for the presence of contaminating RNase, and for activity in the absence of any template to determine whether any of the peak fractions contained MDV.1 RNA.

The peak Q Beta replicase fractions were determined based on the following criteria:
1) fractions that contain 50% +/ 5% of the activity of the maximum fraction;
2) fractions that are free of major RNase contamination; and
3) fractions that are free of MDV-1 RNA contamination.

Fractions meeting these criteria were pooled.

The protein concentration of the fractions were determined using the Bradford Assay. M. Bradford, *Anal. Biochem.*, 72:248 (1976). Replicase activity was determined using the Poly C assay.

An S Sepharose (Pharmacia) column was poured and equilibrated with 10 column volumes of 50 mM Tris-HCl (pH 7.8) 5 mM MgCl2. 5 mM 2.mercaptoethanol, 1 mM EDTA, and 100 mM NaCl.

Once the column was equilibrated, the pooled fraction was diluted with 2.5 volumes of 50 mM Tris-HCl (pH 7.8) 5 mM MgCl$_2$, 5 mM 2.mercaptoethanol, 1 mM EDTA. The diluted enzyme was applied to the column in a concentration of 10 mg of protein per ml of resin at a flow rate of two column volumes per hour. The UV-1 monitor was set at an AUFS setting of 0.5 and the chart speed at 0.2 mm/min.

Once all of the enzyme was applied to the column, the column was washed with 50 mM Tris-HCl (pH 7.8), 5 mM MgCl$_2$, 5 mM 2.mercaptoethanol, 1 mM EDTA, and 100 mM NaCl and a 10 column volume gradient of 100 mM to 400 mM NaCl was run at a flow rate of 1 column volume per hour. Fractions of 0.01 volume of the total gradient were collected. The chart speed of recorder was increased to 0.5 mm/min.

To minimize the risk of contaminating the column fractions with MDV RNA, 0.1 ml aliquots were removed using sterile 1 ml pipettes and transferred to sterile 1.5 ml microcentrifuge tubes.

The S Sepharose fractions were assayed for replicase activity using the Poly C assay, to define the location of the replicase peak.

To discriminate between the enzyme fractions which contain Q Beta "Holoenzyme" versus those that contain Q Beta "alpha-less" enzyme which does not have the S1 subunit and cannot replicate MDV RNA templates, aliquots of the peak fraction were run on denaturing 10–15% poly.

Fractions containing the highest replicase activity were assayed for the presence of contaminating RNases, and were assayed in the absence of any added template to determine whether any of the peak fraction contained MDV.1 RNA.

The "peak" fractions were determined based on the following criteria:
1) fractions that contain at least 33% +/ 5% of the activity of the maximum fraction;
2) fractions that contain only Q Beta "Holoenzyme";
3) fractions that are free of RNase contamination; and
4) fractions that are free of MDV.1 RNA.

Fractions meeting all four of these criteria were pooled. The protein concentration of this fraction was determined using the Bradford Assay. Replicase activity was determined using the Poly C assay.

The fraction was also assayed for replicase activity using MDV RNA as a template.

An equal volume of chilled ultra pure glycerol was added to the remainder of the fraction, and mixed gently until no Schleiren lines were observed.

Q Beta Replicase Assay-Poly C Template

A reaction mixture was prepared by combining the following reagents in a 1.5 ml micro-centrifuge tube at room temperature:

```
 5   μl of 5 × Q beta replicase buffer
 5   μl of 1.0 mg/ml Poly C (Sigma)
 1   μl of 10 mM GTP (Pharmacia)
 1   μl of 50 μg/ml Rifampicin (Sigma)
 0.5 μl of alpha-32P GTP, 10μ Ci/μl (New England Nuclear)
11.5 μl DEPC treated water
 1   μl of enzyme
25   μl total volume
```

The 5×Q Beta replicase buffer consisted of 450 mM Tris-HCl, (pH 7.8), and 70 mM MgCl$_2$.

After all reagents, except the enzyme, had been combined, the tube was vortexed for 10 seconds and then centrifuged at 12,000×g for 2 seconds to get all of the reagents to the bottom of the tube.

The enzyme was added; the tube was mixed gently and incubated for 10 minutes at 37° C.

10 μl aliquots were removed from each reaction tube and pipetted onto DE.81 filters (Whatman). The filters were air dried for 1.2 minutes.

From one of the reaction tubes, 10 μl was removed and pipetted onto a DE.81 filter, allowed to air dry, placed in a scintillation vial containing 3 ml of water and counted. From this data the total number of counts that were added to each tube could be determined.

The filters were transferred to a 1 L beaker containing 200 ml of sodium phosphate (500 mM, pH 7.4) wash buffer. The filters were washed for 20 minutes at room temperature with occasional shaking. The wash solution was decanted and an additional 200 ml of fresh wash buffer solution was added to the beaker and the filters were washed again. The wash step was for 20 minutes. The buffer was removed, and repeated one more time. After the third wash, 200 ml of distilled, deionized water was added to the beaker and the filters were washed for 10 minutes with mixing.

The filters were removed from the water and blotted dry on a piece of Whatman 3 mm paper.

The filters were transferred to scintillation vials (Wheaton) containing 3 ml of water.

The vials were capped and the radioactivity in each vial was determined in a scintillation counter at settings for detection of $^{32}$P, to determine the level of incorporation by each fraction.

Q Beta Replicase Assay-MDV RNA Template

A reaction mixture was prepared by combining the following reagents in a 1.5 ml microcentrifuge tube at room temperature:

---
5 μl of Q Beta replicase buffer
4 μl of a mixture containing 2.5 mM each of ATP, CTP, UTP and GTP (Pharmacia)
1 μl of alpha-$^{32}$P GTP 10μ Ci/μl (New England Nuclear)
9 μl of DEPC treated water
19 μl per assay tube

---

After the reagents had been combined, the tube was vortexed for 10 seconds and centrifuged at 12,000×g for 2 seconds to get all of the contents to the bottom of the tube.

5 μl of an appropriate MDV RNA dilution was added to the above reaction mix. To minimize the risk of contamination, a separate micropipettor was used to dispense the MDV RNA solution. To those reactions where no RNA is added, 5 μl of DEPC-treated water was added.

1 μl of Q Beta replicase was added to above reaction mix, which was mixed gently and incubated 20 minutes at 37° C.

After 20 minutes, 2 μl of reaction was removed and added to 18 μl of 120 mM NaCl—20 mM EDTA and placed on ice.

From one of the reaction tubes, 10 μl was removed and pipetted onto DE-81 filter, allowed to air dry, placed in a scintillation vial contain 3 ml of water, and counted. From this data the total number of counts added to each reaction could be determined.

10 μl of the 20 μl sample from the previous step was pipetted onto a DE-81 filter. The remainder was saved for gel analysis.

The filters were dried for 1-2 minutes, washed and counted as described above for the Poly C assay.

To analyze amplification reaction products on a denaturing polyacrylamide gel, a 6% poly-acrylamide 7 M urea gel was poured and allowed to polymerize The gel was pre-run at 50 W (constant power) for 30 minutes.

1 μl of samples were added to 3 μl of Formamide-Dye loading buffer. The samples were placed in a boiling water bath for 3 minutes, and transferred to ice until loading onto gel.

The samples were run at 50 W (constant power) until the Bromphenol Blue marker had run off the gel.

The gel was dismantled and placed in a cassette on film (Kodak XAR5) overnight at −70° C. with an intensifying screen. The film was developed in an automatic film processor.

The activity of Q Beta replicase produced by the present method is summarized in Table 2.

TABLE 2

Summary of Q Beta Replicase Purification

| Fraction | Units/ml | Total Units | mg/ml | Total mg | U/mg |
|---|---|---|---|---|---|
| Crude Lysate | 190 | 24,700 | 23.5 | 3035 | 8 |
| Q Sepharose | 1013 | 69,900 | 4.25 | 293 | 238 |
| S Sepharose | 670 | 20,100 | 0.59 | 17.7 | 1130 |

1 U = 1 nmol of GMP incorporated in 10 min at 37°

Table 2 shows the recovery of enzyme at each step in the purification process (from 50 g of cells).

The enzyme produced by the present method was incubated in standard amplification assay buffer (90 mM Tris-HCl (pH 7.8) and 14 mM MgCl$_2$) which did not contain any added RNA template and no detectable RNA synthesis was observed after 20 minutes of incubation at 37° C. (FIG. 2, lane 1). MDV.1 RNA was not observed even after 60 minutes of incubation.

Amplification reactions containing the present enzyme were primed with 10$^2$-10$^8$ MDV-Fal-St molecules, (P. M. Lizardi et al., *Biotechnology*, 6:1197-1202 (1988(, and the only product observed was full length MDV-Fal-St (FIG. 2, lanes 2-4). However, when enzyme prepared by the method of Eoyang and August was incubated under the same conditions as above, RNA synthesis was observed in the absence of added RNA template, indicating contamination of the enzyme preparation with MDV.1 RNA.

The resulting material was analyzed on a denaturing polyacrylamide gel, and as shown in FIG. 3, MDV.1 RNA (FIG. 3, lanes 1 and 2) was produced. Furthermore, when amplification reactions containing this enzyme were primed with 10$^2$-10$^8$ MDV-Fal-St molecules, both and Fal-St and MDV-1 RNA were synthesized (FIG. 3, lanes 3-6).

Equivalents

Those skilled in the art will recognize, or be able to ascertain using no more than routine experimentation, many equivalents to the specific embodiments of the invention described specifically herein. Such equivalents are intended to be encompassed in the scope of the following claims.

I claim:
1. A method for purifying Q Beta replicase from cells in which it is produced, comprising the steps of:
   a) disrupting cells which produce Q beta replicase to form a cell lysate;
   b) contacting the cell lysate with polyethyleneimine under conditions appropriate for selective precipitation of nucleic acids present in the lysate, resulting in formation of a supernatant containing Q Beta replicase;
   c) contacting the supernatant with a anionic resin, under conditions appropriate for binding of Q Beta replicase to the resin;
   d) contacting the product of step (c) with a first elution buffer under conditions appropriate for separation of Q Beta replicase from the resin;
   e) contacting the product of step (d) with an cationic resin, under conditions appropriate for binding of Q Beta replicase to the resin; and
   f) contacting the resin of step (e) with a second elution buffer, under conditions appropriate for separation of Q Beta replicase from the resin.

2. A method of claim 1, wherein the cells are *E. coli* cells which produce Q Beta replicase.

3. A method of claim 1, wherein cells are disrupted in step (a) by sonication or homogenization.

4. A method of claim 1, wherein the first elution buffer and the second elution buffer comprise salt gradients having a concentration of NaCl of from about 100 to about 400 mM.

5. A method of producing substantially pure Q Beta replicase, comprising the steps of:
   a) providing a lysate of Q Beta replicase-producing *E. coli* cells;
   b) contacting the cell lysate with a polyethyleneimine in the presence of NaCl under conditions appropriate for selective precipitation of nucleic acids present in the lysate, resulting in formation of a supernatant containing Q Beta replicase;

c) contacting the supernatant with a anionic resin under conditions appropriate for binding of Q Beta replicase to the resin;

d) contacting the product of step (c) with a first elution buffer under conditions appropriate for separation of Q Beta replicase from the resin;

e) contacting the product of step (d) with an cationic resin, under conditions appropriate for binding of Q Beta replicase to the resin; and f) contacting the resin of step (e) with a second elution buffer under conditions appropriate for separation of Q Beta replicase from the resin.

6. A method of claim 5, wherein the polyethyleneimine is 10% (w/v) polyethyleneimine.

* * * * *

UNITED STATES PATENT AND TRADEMARK OFFICE
CERTIFICATE OF CORRECTION

PATENT NO. : 5,141,857
DATED : August 25, 1992
INVENTOR(S) : Robert A. DiFrancesco It is certified that error appears in the above-identified patent and that said Letters Patent is hereby corrected as shown below:

On the title page, item [75] Inventor:

Add co-inventor's Name and Address:

Karin Borcherts, Newton, Mass.

Signed and Sealed this

Seventh Day of September, 1993

Attest:

BRUCE LEHMAN

*Attesting Officer*   *Commissioner of Patents and Trademarks*